United States Patent
Becker et al.

(10) Patent No.: US 10,995,080 B2
(45) Date of Patent: May 4, 2021

(54) STEREOSELECTIVE SYNTHESIS OF PERHYDRO-3,6-DIALKYL-2-BENZO-[B]FURANONES AND ANALOGS

(71) Applicant: International Flavors & Fragrances Inc., New York, NY (US)

(72) Inventors: Yigal Becker, Tel Aviv (IL); Michael Cheskis, Nesher (IL)

(73) Assignee: INTERNATIONAL FLAVOR & FRAGRANCES INC., New York, NY (US)

( * ) Notice: Subject to any disclaimer, the term of this patent is extended or adjusted under 35 U.S.C. 154(b) by 0 days.

(21) Appl. No.: 16/886,009

(22) Filed: May 28, 2020

(65) Prior Publication Data

US 2020/0377466 A1    Dec. 3, 2020

Related U.S. Application Data

(60) Provisional application No. 62/855,074, filed on May 31, 2019.

(51) Int. Cl.
*C07D 307/83*    (2006.01)
*B01J 23/46*    (2006.01)

(52) U.S. Cl.
CPC .......... *C07D 307/83* (2013.01); *B01J 23/462* (2013.01)

(58) Field of Classification Search
CPC .................................................... C07D 307/83
USPC ........................................................... 549/302
See application file for complete search history.

(56) References Cited

PUBLICATIONS

Xie et al., J. Am. Chem. Soc. (2015), 137(11), pp. 3767-3770.*

\* cited by examiner

*Primary Examiner* — Taofiq A Solola
(74) *Attorney, Agent, or Firm* — Licata & Tyrrell P.C.

(57) ABSTRACT

Synthetic methods of preparing perhydro-3,6-dimethyl-2-benzo[b]furanones, in particular dihydromintlactone, and analogs through reaction of dehydrogenation of menthanediols and analogs with a base in the presence of (carbonylchlorohydrido[bis-(2-diphenylphosphinoethyl)amine]ruthenium(II) as catalyst in good stereoselectivity and yields under stereochemistry controlled conditions are disclosed.

20 Claims, No Drawings

STEREOSELECTIVE SYNTHESIS OF PERHYDRO-3,6-DIALKYL-2-BENZO[B]FURANONES AND ANALOGS

CROSS-REFERENCE TO RELATED APPLICATIONS

This application claims priority to U.S. Application Ser. No. 62/855,074 filed May 31, 2019, the content of which is incorporated by reference in its entirety.

FIELD OF THE INVENTION

The present invention is related to the field of flavor and fragrance compounds, in particular, practical synthesis of perhydro-3,6-dimethyl-2-benzo[b]furanones and analogs.

BACKGROUND OF THE INVENTION

Dihydromintlactone (I), namely (+)-(3S,3aS,6R,7aR)-perhydro-3,6-dimethyl-2-benzo[b]furanone, is an important natural flavor and fragrance ingredient, which exhibits strong coumarinic, lactonic, tonka, hay and flouve odor, while its epimer 3-epi-dihydromintlactone (V), namely(+)-(3R,3aS,6R,7aR)-perhydro-3,6-dimethyl-2-benzo[b]furanone), is characterized by a powerful lactonic character.

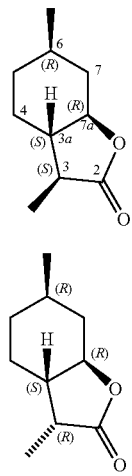

Dihydromintlactone I is more powerful than coumarin and can thus be used in a dose 10 times smaller than that of Coumarin. Due to their high commercial value, practical and economic synthetic methods of these compounds, in particular I, are constantly pursued. Yet, due to the presence of four stereogenic centers in a relatively small molecule, synthesis of the molecule such as dihydromintlactone with control of the desired chirality is challenging.

Gaudin et al. disclosed several routes leading to synthesis of compound I. See U.S. Pat. No. 5,464,824A and Tetrahedron 56, 27, 4769 (2000). According to Scheme 1, (−)-isopulegol (II) is epoxidized by m-chloroperbenzoic acid to give stereoisomeric 1:1 mixture of epoxides which are cleaved by LDA to give a 1:1 mixture of allylic diols. Hydrogenation of the diols affords a 1:1 mixture of (−)-(1R,3R,4S,8R)-3,9-p-menthanediol (III) and (−)-(1R,3R,4S,8S)-3,9-p-menthanediol (IV), which are separated by chromatography or fractional crystallization.

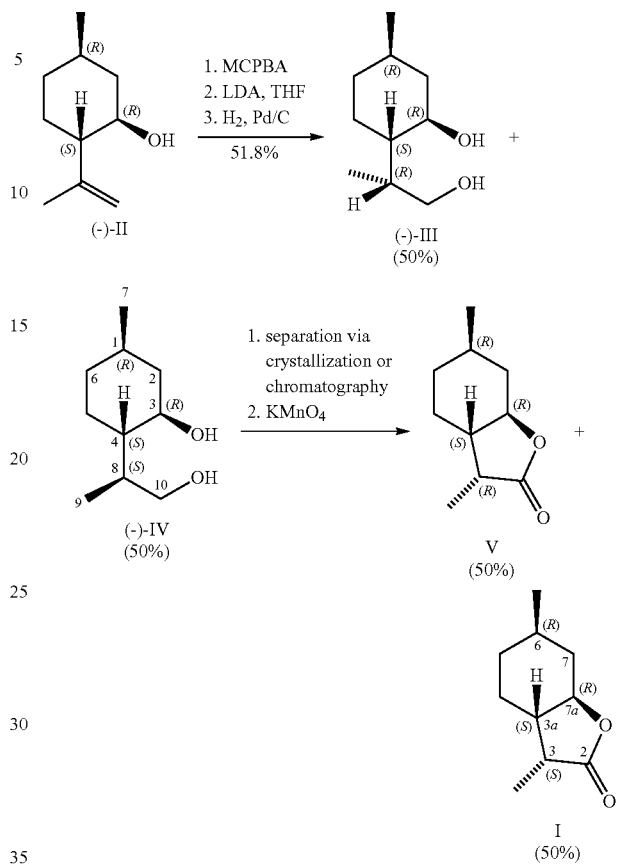

Oxidation of the individual diols gives the corresponding lactones V and I. This method involves four chemical steps and one physical separation step; thus, the desired Compound I is obtained in a low overall yield. Furthermore, oxidation of the diols by potassium permanganate produces a considerable amount of toxic waste containing manganese ions.

A shorter synthesis illustrated in Scheme 2 involves hydroboration-oxidation of (−)-II (see also Helv. Chim Acta, 50 [1] 153 (1967)) to give a mixture of 3,9-p-menthanediols III and IV, in which III predominates. See U.S. Pat. No. 5,464,824A and Tetrahedron 56, 27, 4769 (2000). Separation of the isomers followed by permanganate oxidation affords mainly Compound V. The desired compound I is obtained in a low yield, again with a considerable amount of toxic waste stream containing manganese ions.

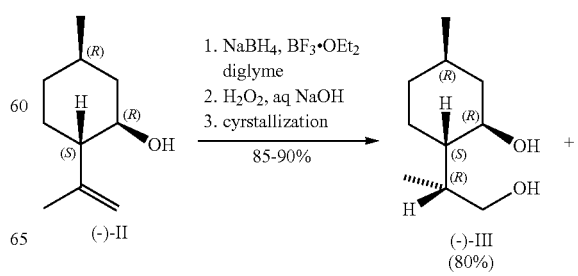

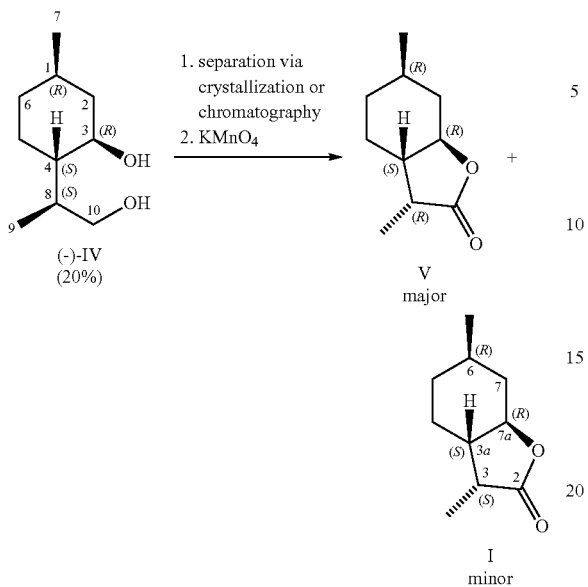

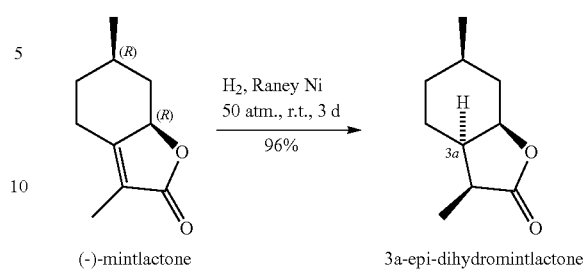

The dehydrogenation of (−)-III was also effected by excess of silver carbonate on Celite® (see Chavan, S. P., et al., Tetrahedron 49(29), 6429 (1993)) or by an excess amount of potassium permanganate-copper sulfate (see Jefford, C. W., et al., Organic Syntheses, Coll. Vol. 9, p. 462 (1998)) to give Compound V as the major product. In addition, these methods generate a considerable amount of heavy metal waste streams and therefore are not suitable for large-scale manufacture. Oxidation of the III-IV mixture by sodium hypochlorite in presence of catalytic amounts of ruthenium chloride according to U.S. Pat. No. 5,106,995A gave dihydromintlactone streoisomers in a composition similar to that obtained from the permanganate oxidation method, in which the undesired V predominates. Catalytic dehydrogenation of the III-IV mixture using $H_2Ru(PPh_3)_4$ (Murahashi et. al, J. Org. Chem. 52[19], 4319 (1987)) or $Ru(PPh_3)_3(CO)H_2$ (Williams et al, Org. Lett., 9, [21] 4387 (2007)) using acetone as hydrogen acceptor also gave similar results. Attempt to dehydrogenate the diols using $RuCl_2[PP_3]_3$ in presence of benzalacetone as acceptor was unsuccessful (Yoshikawa et al, J. Org. Chem. 51[11], 2034 (1986)). Similarly, heterogeneous catalysts such as Ru/alumina or Ru/AlO(OH) (Kim et al., Org. Let. 8[12] 2543 (2006)) were found to be inactive. Copper chromite (U.S. Pat. No. 5,110,954) was found to be an active dehydrogenation catalyst, but the lactones obtained were similar to those from the permanganate and hypochlorite/Ru oxidation methods, where the undesired compound V predominates.

Still another route disclosed by Gaudin, J.-M., et al., involves Raney nickel catalyzed cis-hydrogenation of mintlactone from the less sterically hindered face under 50-atmosphere pressure at room temperature (Scheme 3). See U.S. Pat. No. 5,464,824A and Tetrahedron 56[27] 4769 (2000). However, this method afforded a 3a-epimer of dihydromintlactone.

More recently, Foley, P., et al. disclosed a 5-step synthesis of Compound I as the major isomer in an overall yield of 13.4% starting from isopulegol (Scheme 4). See WO 2017/044957A1. The process involves hazardous reactions such as ozonization, cyanation and chlorination, which generate a considerable amount of toxic effluents and a large amount of aqueous waste stream.

In sum, the existing processes for synthesis of the desired compound I are generally characterized by a low yield of I with a considerable amount of toxic wastes and therefore are not suitable for the economic commercial-scale manufacture. Therefore, an efficient "green" process for practical synthesis of compound I and analogs is still needed.

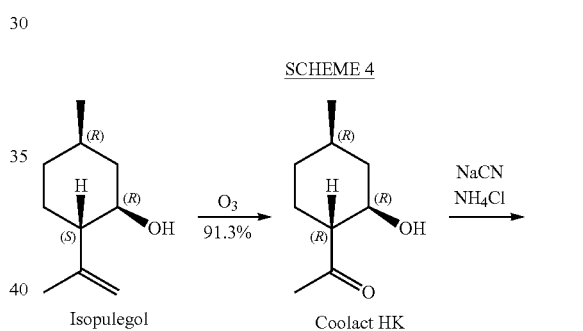

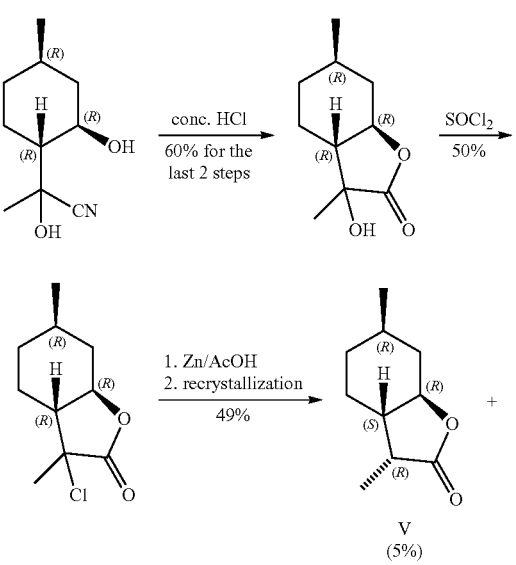

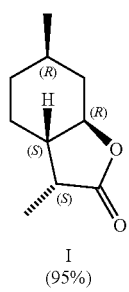

I
(95%)

SUMMARY OF THE INVENTION

It has now been found that the aforementioned disadvantages can be overcome by a one-step, direct dehydrogenation of 3,9-p-menthanediols III and IV in presence of a base and a homogeneous pincer-type catalyst carbonylchlorohydrido[bis-(2-diphenyl-phosphinoethyl)amine]ruthenium(II) (Ru-MACHO®) in an organic solvent. The reaction can be conducted under controlled conditions to produce either Compound I or Compound V as the predominant product. Thus, the present invention fulfills the foregoing need by providing a catalytic stereoselective synthesis of Compound I and analogs under controlled conditions.

In one aspect, the invention provides a process for preparing a lactone compound of formula (A) and (B), comprising dehydrogenation of a diol compound of formula (C) using carbonylchlorohydrido[bis-(2-diphenylphosphinoethyl)amine]ruthenium(II) as a catalyst in the presence of a base in an organic solvent:

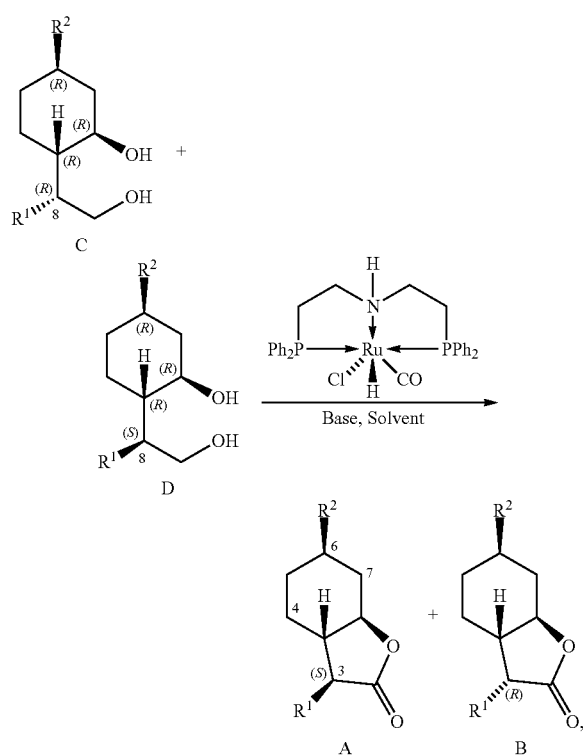

wherein $R^1$ and $R^2$ are each independently alkyl; and wherein either the compound of formula (A) (3-(S)-isomer) or (B) (3-(R)-isomer) is the predominant product by adjusting the conditions of the process.

The process can further comprise isolating the product of formula (A) and/or (B) through extraction, distillation, and/or crystallization of the lactone products.

In a particular embodiment, the invention is directed to a process for preparing (3S,3aS,6R,7aR)-perhydro-3,6-dimethyl-2-benzo[b]furanone (I) and (3R,3aS,6R,7aR)-perhydro-3,6-dimethyl-2-benzo[b]furanone (V) in which I predominates, the method comprising the steps of: (a) mixing an isomeric diol mixture comprised of (1R,3R,4S,8R)-3,9-p-menthanediol (III) and (1R,3R,4S,8S)-3,9-p-menthanediol (IV) in an organic solvent in presence of metal alkoxide (MOR) and (carbonylchlorohydrido[bis-(2-diphenylphosphinoethyl)amine]ruthenium(II) at an elevated temperature through a controlled addition of the catalyst into the reaction mixture at the elevated temperature; and (b) isolating the product, (3S,3aS,6R,7aR)-perhydro-3,6-dimethyl-2-benzo [b]furanone I through extraction and/or distillation.

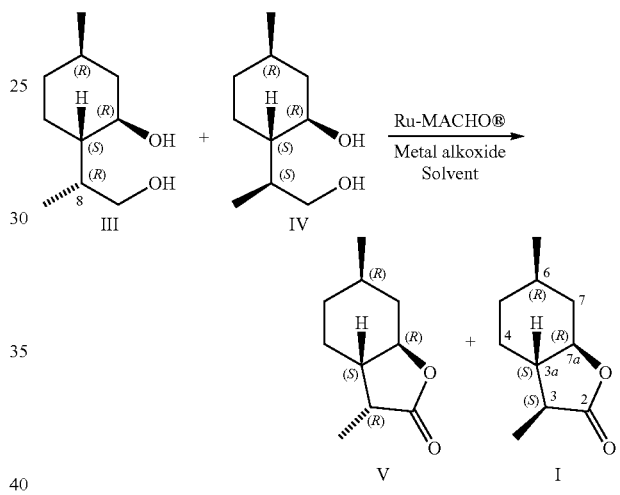

In another particular embodiment, the invention is directed to a process for preparing isomeric (3S,3aS,6R,7aR)-perhydro-3,6-dimethyl-2-benzo[b]furanone (I) and (3R,3aS,6R,7aR)-perhydro-3,6-dimethyl-2-benzo[b]furanone (V) in which V predominates, the method comprising dehydrogenation of an isomeric diol mixture comprised of (1R,3R,4S,8R)-3,9-p-menthanediol (III) and (1R,3R,4S, 8S)-3,9-p-menthanediol (IV), in which the compound III predominates, in an organic solvent in presence of a metal alkoxide and (carbonylchlorohydrido[bis-(2-diphenylphosphinoethyl)amine]ruthenium(II) by heating the reaction mixture containing the catalyst gradually to an elevated temperature.

The invention allows economic manufacture of dihydromintlactone (hexahydro-3,6-dimethyl-2(3H)-benzofuranone), known under the trade name Koumalactone®. Starting from citronellal, dihydromintlactone can be synthesized in three steps at a considerably lower cost than the market price. The invention is based on a novel dehydrogenation-epimerization process carried out in the presence of a unique homogeneous pincer-type catalyst carbonylchlorohydrido[bis-(2-diphenylphosphinoethyl)amine]ruthenium(II) (Ru-MACHO®, of Takasago International Corporation) using a metal alkoxide as base.

In addition, while commercial dihydromintlactone is a racemate supplied as 10% solution in TEC, the invention allows the manufacture of the neat ingredient in both racemic and optically active forms. Furthermore, variation of the reaction conditions can be used for the manufacture of another commercial diastereoisomeric dihydromintlactone composition known as Natactone®.

Moreover, the present invention can be modified and optimized to produce a commercial product containing dihydromintlactone/3-epi-dihydromintlactone in various desired ratios by varying the process conditions.

Other benefits and advantages of the present invention can be better appreciated through the following detailed description, examples, and claims.

DETAILED DESCRIPTION OF THE INVENTION

The present invention is based on a surprising discovery that catalytic dehydrogenation of a 3,9-p-menthanediols (III-IV) mixture by carbonylchlorohydrido[bis-(2 diphenylphosphinoethyl)amine]ruthenium(II) (Ru-MACHO®) affords preferentially (3S,3aS,6R,7aR)-perhydro-3,6-dimethyl-2-benzo[b]furanone (I) in a high selectivity and yield, accompanied by a small amount of its 3-epimer (3R,3aS,6R,7aR)-perhydro-3,6-dimethyl-2-benzo[b]furanone (V). See Scheme 5.

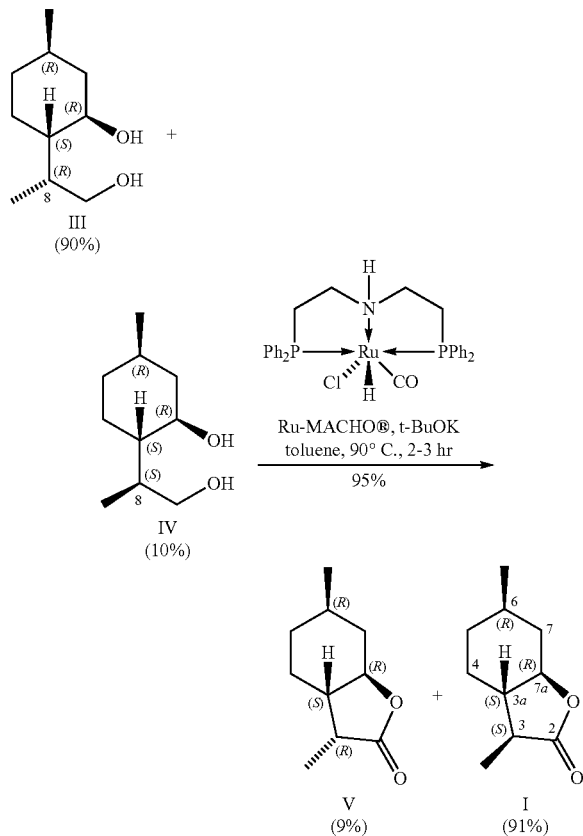

Thus, during the dehydrogenation the R configuration on C8 of III is inverted, leading to I having the desired S configuration at the 3-position. Consequently, the III-IV mixture is smoothly transformed to a mixture of I:V in a ratio of 91:9 and in 95% overall yield.

Although the efficient dehydrogenation of 1,4-diols to lactones by Ru-MACHO® has been reported (see U.S. Pat. No. 9,000,212B2), the inversion of configuration on C8 during dehydrogenation is unprecedented.

While not intending to be bound by theory, a plausible mechanism assumes faster primary alcohol dehydrogenation at C10 than the secondary alcohol at C3. The 8R-aldehyde VI thus formed racemizes at C8 through equilibration with the enol form VII, with VII being thermodynamically more favored. The latter is believed to be coordinated to a ruthenium species at the less sterically hindered face. Antiperiplanar attack of C3 hydroxyl on the coordinated enol affords the 8S-Lactol VIII, which is rapidly dehydrogenated to I. See Scheme 6.

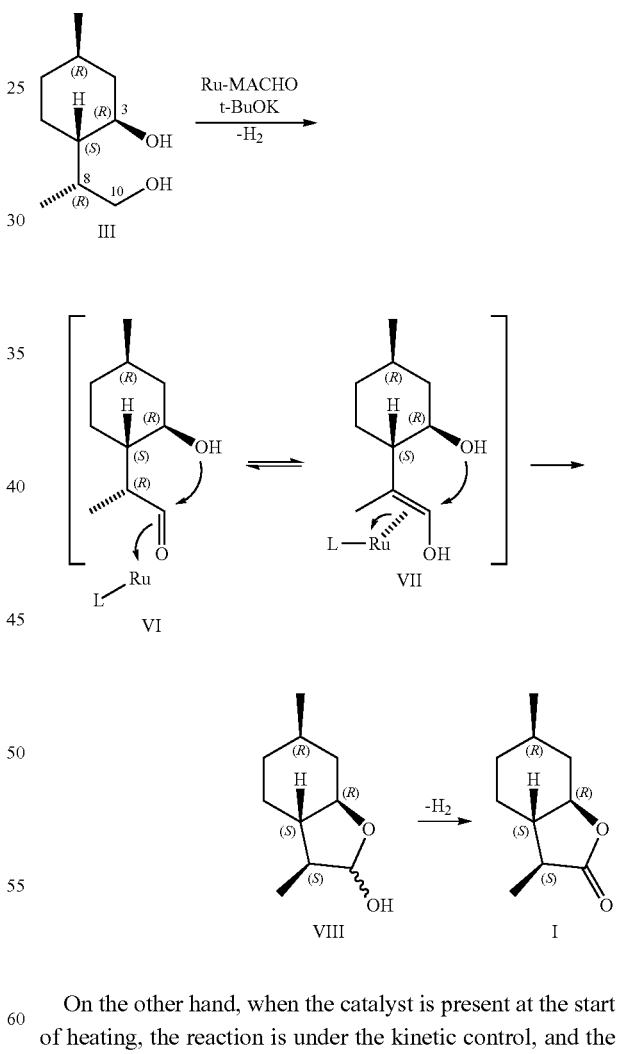

On the other hand, when the catalyst is present at the start of heating, the reaction is under the kinetic control, and the equilibrium between VI and VII may not be established before the aldehyde intermediate VI is converted to lactol intermediate IX, thus retaining the stereochemistry at the 8-position to form the product V as the major product. See Scheme 7.

SCHEME 7

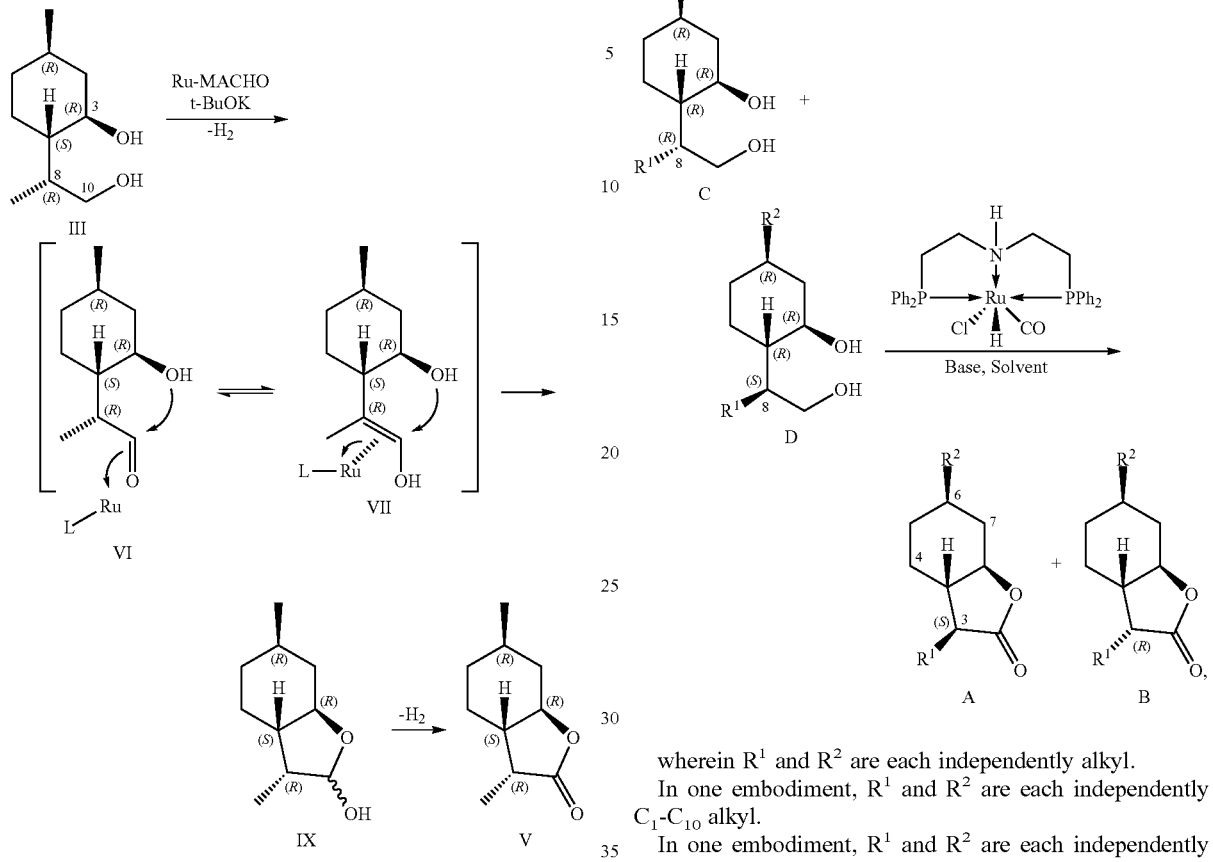

Thus, in order to obtain a composition rich in I in a high selectivity, the solution of the catalyst in toluene is gradually added to III-IV mixture containing potassium tert-butoxide in boiling toluene. The isomeric composition obtained can be enriched with I to match commercially available composition Natactone®.

The reaction is performed by heating 3,9-p-menthanediols in presence of potassium t-butoxide in an organic solvent to an elevated temperature, and while maintaining at the elevated temperature, adding catalyst carbonylchlorohydrido[bis-(2-diphenylphosphinoethyl)amine]ruthenium(II) gradually into the reaction mixture until all the starting material has been substantially converted to the product.

On the other hand, it has also been discovered surprisingly that if the diols III-IV, Ru-MACHO® and potassium tert-butoxide are dissolved in toluene and the mixture is gradually heated to 80-90° C., then the compound V predominates.

Thus, in one aspect, the present invention provides a method of preparing a lactone compound of formula (A) or (B), comprising dehydrogenation of a diol compound of formula (C) and/or (D) using carbonylchlorohydrido[bis-(2-diphenylphosphinoethyl)amine]ruthenium(II) as a catalyst in the presence of a base in an organic solvent:

wherein $R^1$ and $R^2$ are each independently alkyl.

In one embodiment, $R^1$ and $R^2$ are each independently $C_1$-$C_{10}$ alkyl.

In one embodiment, $R^1$ and $R^2$ are each independently $C_1$-$C_4$ alkyl.

In one embodiment, $R^1$ and $R^2$ are both methyl.

In some embodiments, the compound of formula (A) (3-(S)-isomer) is the predominant product, and the method comprises adding the catalyst into a mixture of the diol compound of formula (C) and/or (D) and the base in the organic solvent gradually at an elevated temperature.

In some embodiments, the compound of formula (B) (3-(R)-isomer) is the predominant product, and the method comprises heating a mixture of the diol compound of formula (C), the catalyst, and the base in the organic solvent gradually to an elevated temperature.

In some embodiments, sometimes preferably, the base is a metal alkoxide.

In some embodiments, the base is selected from the group consisting of sodium methoxide, sodium ethoxide, sodium isopropoxide, sodium butoxide, sodium sec-butoxide, sodium tert-butoxide, sodium tert-pentoxide, and potassium tert-butoxide In some embodiments, sometimes preferably, the base is potassium tert-butoxide (KOBu$^t$) or sodium tert-butoxide (NaOBu$^t$).

In some embodiments, the amount of metal alkoxide is about 0.5 mol % to one or more molar equivalents relative to the total amount of diol compounds C and D.

In some embodiments, sometimes preferably, the metal alkoxide is in the range of about 0.5 to 10 mol % of the total amount of diol compounds C and D.

In some embodiments, the metal alkoxide is in the range of about 1 to 5 mol % of the total amount of diol compounds C and D.

In some embodiments, the metal alkoxide is in the range of about 2 to 3 mol % of the total amount of diol compounds C and D.

In some embodiments, the organic solvent is selected from the group consisting of straight-chain or branched hydrocarbons, straight-chain or branched halohydrocarbons, aromatic hydrocarbons, aromatic halohydrocarbons, open-chain or cyclic ethers, and ketones.

In some embodiments, the organic solvent is selected from the group consisting of hexanes, heptanes, isooctane, benzene, toluene, xylenes, dichloroethane, chlorobenzene, dichlorobenzenes, terahydrofuran, 1,6-dioxane, acetone, butanone, and methyl isobutyl ketone.

In some embodiments, sometimes preferably, the organic solvent is toluene.

In some embodiments, the elevated temperature is from 50° C. to 140° C., or a reflux temperature of the organic solvent.

In some embodiments, the elevated temperature is from 60° C. to 115° C., or a reflux temperature of the organic solvent.

In some embodiments, the elevated temperature is from 70° C. to 95° C., or a reflux temperature of the organic solvent In some embodiments, the carbonylchlorohydrido[bis-(2-diphenylphosphinoethyl)amine]ruthenium(II) catalyst is in an amount of about 0.0001 mol % to about 5 mol % of the compound of formula C and/or D.

In some embodiments, the carbonylchlorohydrido[bis-(2-diphenylphosphinoethyl)amine]ruthenium(II) catalyst is in an amount of about 0.0005 mol % to about 2.5 mol % of the compound of formula C and/or D.

In some embodiments, the carbonylchlorohydrido[bis-(2-diphenylphosphinoethyl)amine]ruthenium(II) catalyst is in an amount of about 0.001 mol % to about 1.0 mol % of the compound of formula C and/or D.

In a particular embodiment, the carbonylchlorohydrido[bis-(2-diphenylphosphinoethyl)amine]ruthenium(II) catalyst is in an amount of about 0.01 mol % of the compound of formula C and/or D.

In some embodiments, the method further comprises isolating the compound of formula A and/or B through extraction, and/or distillation, and/or crystallization from the reaction mixture.

In some embodiments, the isolating comprises the steps of: (a) washing the reaction mixture with water or an aqueous solution to remove inorganic salts; (b) removing the organic solvent by evaporation to obtain a crude product; and (c) distilling or crystallizing the compound of formula A and/or B out of the crude product.

In one particular embodiment, the present invention provides a process for preparing (3S,3 aS,6R,7aR)-perhydro-3,6-dimethyl-2-benzo[b]furanone (I) and (3R,3 aS,6R,7 aR)-perhydro-3,6-dimethyl-2-benzo[b]furanone (V) in which I predominates, the process comprising the steps of:

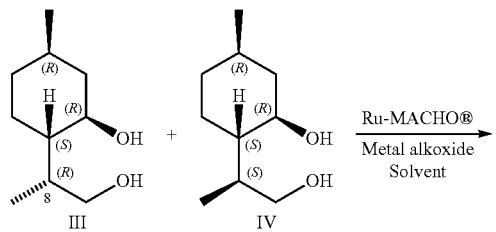

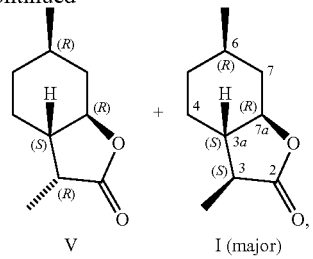

(a) heating a reaction mixture comprising (1R,3R,4S,8R)-3,9-p-menthanediol (III) and/or (1R,3R,4S,8S)-3,9-p-menthanediol (IV) and a metal alkoxide (MOR) in an organic solvent to an elevated temperature while stirring;
(b) adding a catalytic amount of (carbonylchlorohydrido[bis-(2-diphenylphosphinoethyl)amine]ruthenium(II) into the reaction mixture at the elevated temperature; and
(c) stirring the reaction mixture at the elevated temperature until the diol compounds (III) and/or (IV) are substantially or completely converted.

In this embodiment, the compound I can be obtained predominantly under controlled conditions regardless of the composition molar ratios of the starting materials III and IV.

In some embodiments, the process further comprises isolating the product, (3S,3aS,6R,7aR)-perhydro-3,6-dimethyl-2-benzo[b]furanone (I), through extraction and/or distillation from the reaction mixture.

In another particular embodiment, the present invention provides a process for preparing isomeric (3S,3aS,6R,7aR)-perhydro-3,6-dimethyl-2-benzo[b]furanone (I) and (3R,3aS,6R,7aR)-perhydro-3,6-dimethyl-2-benzo[b]furanone (V) in which V predominates, the process comprises the steps of:
(a) heating a reaction mixture comprising (1R,3R,4S,8R)-3,9-p-menthanediol (III), a metal alkoxide, and a catalytic amount of (carbonylchlorohydrido[bis-(2-diphenylphosphinoethyl)amine]ruthenium(II) in an organic solvent gradually to an elevated temperature while stirring; and (b) stirring the reaction mixture until all the (1R,3R,4S,8R)-3,9-p-menthanediol (III) is substantially or completely converted.

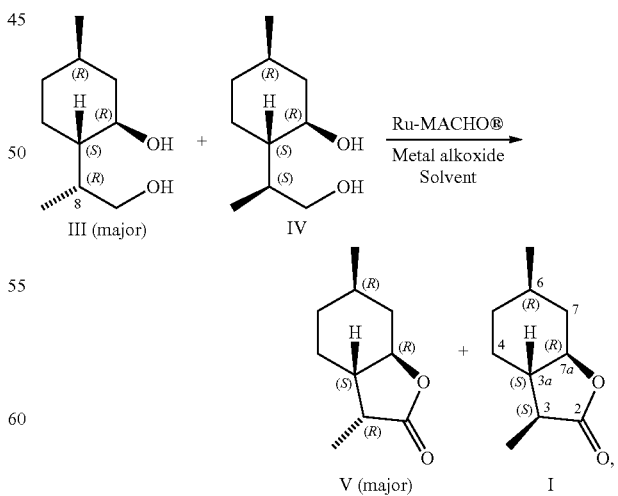

In some embodiments, the (1R,3R,4S,8R)-3,9-p-menthanediol (III) comprises a minor amount of isomer (1R,3R,4S,8S)-3,9-p-menthanediol (IV).

In some embodiments, the process further comprises isolating the product, (3R,3aS,6R,7aR)-perhydro-3,6-dimethyl-2-benzo[b]furanone (V), through extraction and/or distillation.

In some embodiments, sometimes preferably, the metal alkoxide is potassium tert-butoxide (KOBu$^t$) or sodium tert-butoxide (NaOBu$^t$).

In some embodiments, the metal alkoxide is in the range of about 0.5 to 10 mol % of the total amount of (1R,3R,4S,8R)-3,9-p-menthanediol (III) and/or (1R,3R,4S,8S)-3,9-p-menthanediol (IV).

In some embodiments, the metal alkoxide is in the range of about 1 to 5 mol % of the total amount of (1R,3R,4S,8R)-3,9-p-menthanediol (III) and/or (1R,3R,4S,8S)-3,9-p-menthanediol (IV).

In some embodiments, the metal alkoxide is in the range of about 2 to 3 mol % of the total amount of (1R,3R,4S,8R)-3,9-p-menthanediol (III) and/or (1R,3R,4S,8S)-3,9-p-menthanediol (IV).

In some embodiments, sometimes preferably, the organic solvent is toluene.

In some embodiments, the elevated temperature is from 60° C. to 115° C.

In some embodiments, the quantity of (carbonylchlorohydrido[bis-(2-diphenylphosphinoethyl)amine]ruthenium (II) is in the range from 0.0005 mol % to 2.5 mole %, preferably from 0.001 mol % to 1 mol % relative to the total amount of (1R,3R,4S,8R)-3,9-p-menthanediol (III) and/or (1R,3R,4S,8S)-3,9-p-menthanediol (IV).

In some embodiments, the quantity of (carbonylchlorohydrido[bis-(2-diphenylphosphinoethyl)amine]ruthenium (II) is about 0.01 mole % the total amount of (1R,3R,4S,8R)-3,9-p-menthanediol (III) and/or (1R,3R,4S,8S)-3,9-p-menthanediol (IV).

Other conditions and procedures described above and/or in the Examples below are applicable and/or adaptable to the process of preparation herein.

EXAMPLES

The following examples serve to illustrate the invention, without restricting it in any way.

Example 1

Fifty grams (287.34 mmol) of (1R,3R,4S,8R)-3,9-p-menthanediol (III) and (1R,3R,4S,8S)-3,9-p-menthanediol (IV) having the ratio of 89.4:10.0 respectively was added to potassium tert-butoxide (0.88 g, 7.7640 mmol) followed by toluene (230.0 g). The mixture was heated to reflux, and then Ru-MACHO® (0.0161 g, 0.0264 mmol, 0.009 mol %) in toluene (36 g) was added during 10 min. The reaction mixture was stirred under reflux for 3 hours. According to GC analysis the reaction mixture contained I (89.0%) and V (9.0%). The reaction mixture was cooled, washed twice with water (50 ml) and evaporated under reduced pressure to give an oily residue. The oil was subjected to flash distillation to give 47.0 g of colorless liquid having isomers content of 89% I and 9% III. The molar yield of the lactonic mixture is 95%.

Example 2

(−)-Isopulegol ex Sigma [α]$_D^{20}$=−21° (neat) was converted to optically active crystalline diols according to Helv. Chim Acta 50 [1] 153 (1967). The ratio of III:IV was 85:15 having [α]$_D^{20}$=−23.57° (10% in CHCl$_3$). The diols were dehydrogenated using the method according to Example 1 to give (+)-I (89.3%) and (+)-V (8.8%) having [α]$_D^{20}$=+26.6° (C=1.25%, CHCl$_3$).

Example 3

A mixture of diols III-IV (0.5948 g, isomers ratio 85:15 respectively) was added to potassium tert-butoxide (0.0197 g) followed by addition of toluene (3.8 g) and the mixture was heated to 90° C. (bath temperature). Then Ru-MACHO® (0.0012 g) in toluene (1.5 g) was added during 10 min. The reaction mixture was stirred for 45 minutes. At this point GC analysis indicated that the content of I was 71.3% and V content was 6.4%. Heating was continued for additional 45 minutes. GC analysis indicated that the content of I was 86.8% and V content was 8.4%.

Example 4

A mixture of diols III-IV (0.2932 g, isomers ratio 85:15 respectively) was added to potassium tert-butoxide (0.0104 g) followed by addition of Ru-MACHO® (0.0058 g) and toluene (4.09 g). The reaction mixture was gradually heated from 20° C. to 90° C. during 30 minutes, followed by heating at 90° C. (bath temperature) for 105 minutes. GC analysis indicated that the content of I was 21.9% and V content was 65.5%. The reaction mixture contained 11.3% unreacted diols.

Example 5

A mixture of III-IV (18.5 g, isomers ratio 85:15 respectively), potassium tert-butoxide (0.5 g), and Ru-MACHO® (0.0720 g) was dissolved in toluene (330 g). The reaction mixture was stirred and heated to 91° C. (oil bath) for 0.5 hour followed by further heating at the same temperature for 0.5 hr. Then the temperature was gradually raised to 107° C. (oil bath) followed by stirring at this temperature for 1 hr. The stirred reaction mixture was cooled to 30° C. followed by the addition of water (50 mL). The phases were separated and the toluene phase was washed with an additional portion of water (50 mL). After solvent distillation under reduced pressure there was obtained pale yellow oil (15.7 g, lactone content of 99.4%) having isomers ratio (wt %) I:V=37.7:61.7. The molar yield of the two isomers is 87.2%.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

The term "about" generally includes up to plus or minus 10% of the indicated number. For example, "about 10%" may indicate a range of 9% to 11%, and "about 20" may mean from 18 to 22. Alternatively, "about" includes up to plus or minus 5% of the indicated value. Other meanings of "about" may be apparent from the context, such as rounding off, so, for example "about 1" may also mean from 0.5 to 1.4.

All publications cited herein are incorporated by reference in their entirety for all purposes.

It should be understood that embodiments described herein should be considered as illustrative only, without limiting the scope of the invention. While several embodiments have been described in the Examples above, it will be understood by those of ordinary skill in the art that various changes in form and details may be made therein without departing from the spirit and scope of the disclosure as defined by the following claims.

What is claimed is:

1. A method of preparing a lactone compound of formula (A) or (B), comprising dehydrogenation of a diol compound of formula (C) and/or (D) using carbonylchlorohydrido[bis-(2-diphenylphosphinoethyl)amine]ruthenium(II) as a catalyst in the presence of a base in an organic solvent:

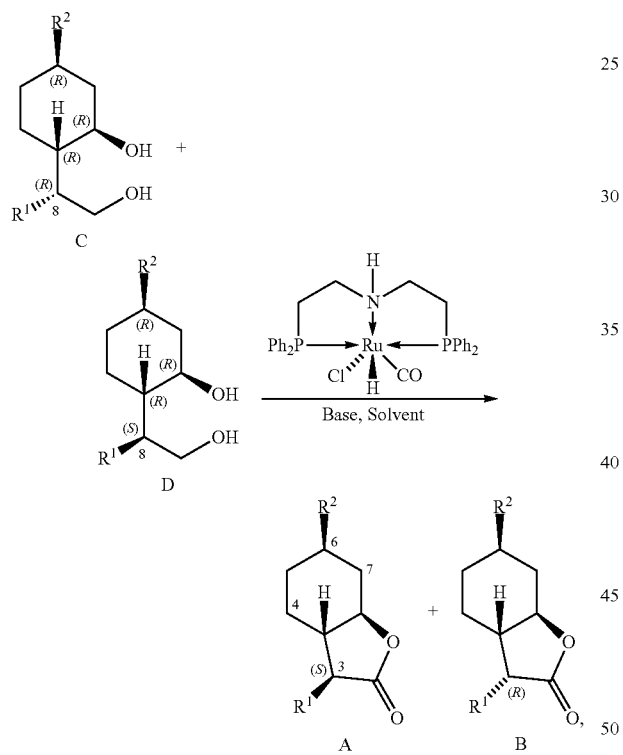

wherein $R^1$ and $R^2$ are each independently alkyl.

2. The method of claim 1, wherein $R^1$ and $R^2$ are each independently $C_1$-$C_{10}$ alkyl.

3. The method of claim 1, wherein $R^1$ and $R^2$ are both methyl.

4. The method of claim 1, wherein the compound of formula (A) (3-(S)-isomer) is the predominant product, the method comprising adding the catalyst into a mixture of the diol compound of formula (C) and/or (D) and the base in the organic solvent at an elevated temperature.

5. The method of claim 1, wherein the compound of formula (B) (3-(R)-isomer) is the predominant product, the method comprising heating a mixture of the diol compound of formula (C), the catalyst, and the base in the organic solvent to an elevated temperature.

6. The method of claim 1, wherein the base is a metal alkoxide.

7. The method of claim 6, wherein the metal alkoxide is selected from the group consisting of sodium methoxide, sodium ethoxide, sodium isopropoxide, sodium butoxide, sodium sec-butoxide, sodium tert-butoxide, sodium tert-pentoxide, potassium tert-butoxide, and combinations thereof.

8. The method of claim 6, wherein the amount of metal alkoxide is about 0.5 0.5 to 10 mol % of the total amount of diol compounds C and D.

9. The method of claim 1, wherein the organic solvent is selected from the group consisting of straight-chain or branched hydrocarbons, straight-chain or branched halohydrocarbons, aromatic hydrocarbons, aromatic halohydrocarbons, open-chain or cyclic ethers, and ketones.

10. The method of claim 1, wherein the organic solvent is selected from the group consisting of hexanes, heptanes, isooctane, benzene, toluene, xylenes, dichloroethane, chlorobenzene, dichlorobenzenes, terahydrofuran, 1,6-dioxane, acetone, butanone, and methyl isobutyl ketone.

11. The method of claim 4, wherein the elevated temperature is from 50° C. to 140° C., or a reflux temperature of the organic solvent.

12. The method of claim 1, wherein the carbonylchlorohydrido[bis-(2-diphenylphosphinoethyl)amine]ruthenium (II) catalyst is in an amount of about 0.0001 mol % to about 5 mol % of the compound of formula C and/or D.

13. A process for preparing (3S,3aS,6R,7aR)-perhydro-3,6-dimethyl-2-benzo[b]furanone (I) and (3R,3aS,6R,7aR)-perhydro-3,6-dimethyl-2-benzo[b]furanone (V) in which I predominates, comprising the steps of:

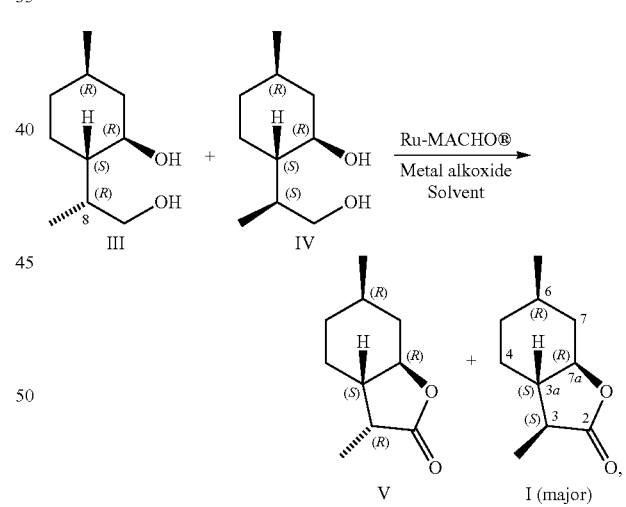

(a) heating a reaction mixture comprising (1R,3R,4S,8R)-3,9-p-menthanediol (III) and/or (1R,3R,4S,8S)-3,9-p-menthanediol (IV) and a metal alkoxide (MOR) in an organic solvent to an elevated temperature;

(b) adding a catalytic amount of (carbonylchlorohydrido[bis-(2-diphenylphosphinoethyl)amine]ruthenium(II) into the reaction mixture at the elevated temperature; and (c) stirring the reaction mixture at the elevated temperature until the diol compounds (III) and/or (IV) are substantially or completely converted.

14. A process for preparing isomeric (3S,3aS,6R,7aR)-perhydro-3,6-dimethyl-2-benzo[b]furanone (I) and (3R,3aS,6R,7aR)-perhydro-3,6-dimethyl-2-benzo[b]furanone (V) in which V predominates, the process comprising the steps of: (a) heating a reaction mixture comprising (1R,3R,4S,8R)-3,9-p-menthanediol (III), a metal alkoxide, and a catalytic amount of (carbonylchlorohydrido[bis-(2-diphenylphosphinoethyl)amine]-ruthenium(II) in an organic solvent to an elevated temperature; and (b) stirring the reaction mixture until all the (1R,3R,4S,8R)-3,9-p-menthanediol (III) is substantially or completely converted.

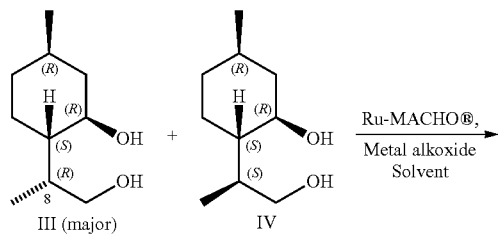

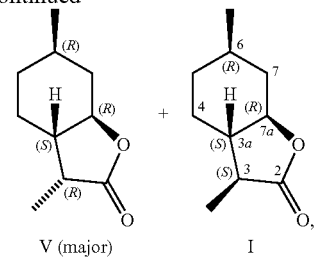

15. The process of claim 14, wherein the (1R,3R,4S,8R)-3,9-p-menthanediol (III) comprises a minor amount of isomer (1R,3R,4S,8S)-3,9-p-menthanediol (IV).

16. The process of claim 14, wherein the metal alkoxide is potassium tert-butoxide (KOBu$^t$) or sodium tert-butoxide (NaOBu$^t$).

17. The process of claim 14, wherein the metal alkoxide is in the range of about 0.5 to 10 mol % of (1R,3R,4S,8R)-3,9-p-menthanediol.

18. The process of claim 14, wherein the organic solvent is toluene.

19. The process of claim 14, wherein the elevated temperature is from 60° C. to 115° C.

20. The process of claim 14, wherein the quantity of (carbonylchlorohydrido[bis-(2-diphenylphosphinoethyl)amine]ruthenium(II) is in the range from 0.0005 mol % to 2.5 mole %, preferably from 0.001 mol % to 1 mol %.

* * * * *